United States Patent [19] [11] 4,271,141
Goedemans [45] Jun. 2, 1981

[54] RADIOIMMUNOLOGICAL METHOD OF DETERMINING THE THYROID FUNCTION BY AN IN VITRO TEST IN BLOOD SERUM

[75] Inventor: Wilhelmus T. Goedemans, Schoorl, Netherlands

[73] Assignee: Byk-Mallinckrodt CIL B.V., Petten, Netherlands

[21] Appl. No.: 968,591

[22] Filed: Dec. 11, 1978

[30] Foreign Application Priority Data

Dec. 16, 1977 [NL] Netherlands ................. 7713952

[51] Int. Cl.$^3$ ............... G01N 33/48; G01T 1/00; A01K 43/00
[52] U.S. Cl. ..................................... 424/1; 424/12; 23/230 B
[58] Field of Search ................ 424/1, 12; 23/230 B; 422/61

[56] References Cited
U.S. PATENT DOCUMENTS 3,666,854 5/1972 Eisentraut ........................ 424/1
3,911,096 11/1975 Chopra ............................ 424/1
4,066,410 1/1978 Eisentraut ........................ 424/1

Primary Examiner—Brooks H. Hunt
Assistant Examiner—Christine M. Nucker
Attorney, Agent, or Firm—Bernard & Brown

[57] ABSTRACT

The present invention provides an improved method for determining the thyroid function by means of an in vitro test using blood serum. Such a method involves an improvement of the procedure whereby (a) a patient's blood serum sample is mixed with a solution containing radioactive thyroxine and with a compound that liberates thyroxine from thyroxine-binding globulin; (b) the test mixture is buffered to achieve proper conditions for carrying out a thyroxine-binding immunoreaction; (c) an antiserum is added to provide antibodies which bind a portion of the thyroxine present by means of such a thyroxine-binding immunoreaction; (d) unbound thyroxine is thereafter separated from the antibody-bound thyroxine; and (e) the relative quantities of bound and unbound thyroxine are then determined by measurement of radioactivity.

In accordance with the present invention, such a procedure is improved by adding to the test mixture, after it has been appropriately buffered, a second additional sample of the patient's blood serum. This second sample of the patient's serum acts as a "correcting" or "normalizing" second binding agent, the addition of which improves the accuracy of thyroid function determination by means of the radioimmunoassay procedure.

5 Claims, 2 Drawing Figures

RADIOIMMUNOLOGICAL METHOD OF DETERMINING THE THYROID FUNCTION BY AN IN VITRO TEST IN BLOOD SERUM

The invention relates to a method of determining the thyroid function by an in vitro test in blood serum in which a blood serum sample of a patient is mixed with a solution containing radioactive thyroxine and with a compound which liberates thyroxine from thyroxine-binding globulin (TBG), buffering the mixture with a buffering agent, adding an antiserum containing antibodies for an immunoreaction with thyroxine, separating the nonbound thyroxine from the thyroxine bound to antibodies and determining their relative quantities by measurements of the radioactivity.

Figure 1:
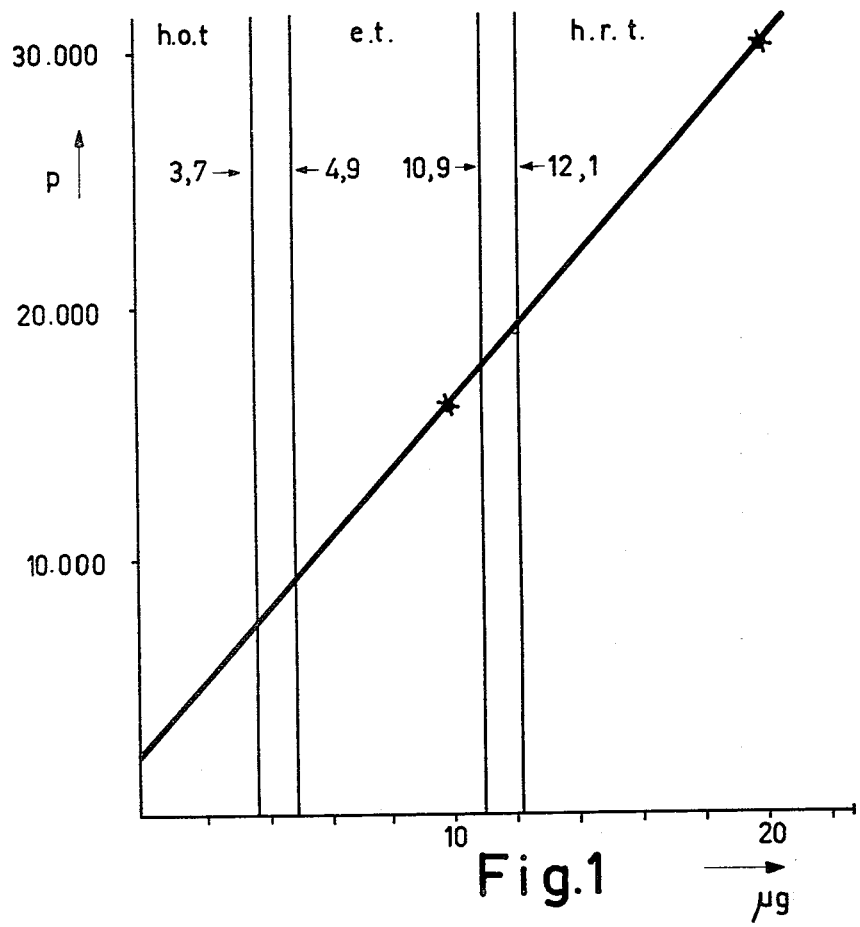
FIG. 1 illustrates a standard curve showing the relationship between radioactivity and concentration of thyroxine in standard samples when such standard samples are treated in accordance with the procedures of Example 1.

The in vitro determination of thyroxine in blood serum is of importance in order to carry out an investigation into the thyroid action.

Such a determination can be carried out in one of a number of ways. However, in view of the accuracy of the result obtained, the aforesaid method is nowadays mainly used, which method is termed, "The radioimmunoassay method".

A recent radioimmunoassay method is described in the published Netherlands Patent application No. 7605447. In this method a special antiserum is used which enters into a specific immunoreaction with thyroxine. Although this method has an improved reproducibility than the previously used methods, it nevertheless appears in practice that the results obtained are not in agreement with the clinical condition of the patient. This is because the content of TBG, the protein to which thyroxine is substantially entirely bound to, can vary considerably. For example, TBG in an increased concentration is present if the estrogen level is increased and a TBG decrease occurs when the concentrations of androgenic anabolic steroids are increased. In other words, the overall thyroxin concentration can be increased or reduced as a result of variations in the TBG content. This may result in misinterpretation of the result and hence in an incorrect diagnosis as regards the thyroid function. In fact, the action of the thyroid gland is determined by the quantity of free thyroxine in the blood, that is thyroxine not bound to TBG. The addition of the second or other sample quantity of patient's blood serum may take place, for example, simultaneously with the addition of the antiserum.

The TBG present in this blood serum competes with the added antibody in binding thyroxine. As a result of this, the results obtained by measuring the radioactivity after the usual incubation and separation, are also determined by the thyroxine binding capacity of the patient serum. For example, the corrected thyroxin determination is a good reflection of the small quantity of free thyroxine which is present in the blood. As a result of this, a better insight in the thyroid function is obtained than when the total amount overall of thyroxine is determined.

Such a correction or normalization is described by Ashkar and Bezjian (JAMA 221 (1972), 1483–85), in which, however, no antiserum is used for an immunoreaction with thyroxine but thyroxine-binding globulin; such a binding reaction is less specific and is more frequently disturbed, for example, by certain medicines in the blood. It is therefore surprising that in a field in which there is much activity and on which annually many publications are issued, a corrected radioimmunoassay method has been unknown more than five years after the above-mentioned normalization method.

The quantity of patients serum to be added afterwards does not lie between narrow limits. An addition of from 10 to 60% by volume with respect to the initial quantity of blood serum, preferably from 15 to 25% by volume, is sufficient for the desired correction. Addition of a larger quantity of blood serum would remove too much thyroxine so that insufficient radioactivity would remain after the separation.

After the usual incubation period which, dependent on the antiserum used, generally is from 0.5 to 2 hours, the non-bound thyroxine is separated from the bound thyroxine. This separation can be carried out according to known methods. For example, the separation may be carried out by means of activated charcoal, polyethylene glycol or an ion exchanger, or by precipitating thyroxine with a second antibody, ethanol or ammonium sulphate. Another separation means suitable for this purpose is a crosslinked dextran, viz. Sephadex (registered trade mark) which is present, for example, in a column. Test tubes containing thyroxine-binding antibodies adhered to the inside may alternatively be used for the separation. In both cases a competition reaction takes place with the thyroxine present between on the one hand the antibodies present in the added antiserum and on the other hand the thyroxine-binding substances present in the separating medium.

Ultimately, the relative quantities of radioactive thyroxine bound to the separation medium are determined. This may be carried out by measuring the radioactivity of, for example, the Sephadex column or the test tube used, after thorough eluation or rinsing. The measured radioactivity is a measure of the quantity of thyroxine in the blood serum. A standard curve is used to find this thyroxine concentration. The curve is obtained by measuring the radioactivity of a few standard sera of which the thyroxine concentrations are known, then plotting in a graph the thyroxin concentrations against the radiactivity found, and finally drawing a line between the found points.

In the initial quantity of patient serum the thyroxine must be liberated from the TBG. This may be done by means of reagents known for this purpose, preferably sodium hydroxide solution. The buffering, that is bringing the mixture of a pH of approximately 8.6, may be carried out with an organic acid; preferably barbital is used for this purpose combined with the sodium salt thereof in an aqueous solution. As a radioactive thyroxine is used thyroxin marked with $^{125}I$.

The antiserum the antibodies of which enter into a specific immunoreaction with throxine can be prepared by immunisation of animals, preferably goats, sheep, rabbits or guinea-pigs, with thyroxine-albumin conjugate formulated in Freun complete adjuvant (see P. C.

Bartels, W. Th. Goedemans and A. F. M. Roijers; Clin, Chim, Acta., 81 (1977), 63–73)

Embodiments of the invention will now be described in greater detail with reference to the following specific Examples.

EXAMPLE 1

A barbital buffer solution is prepared by dissolving 15.45 g of sodium salt of 5,5′-diethylbarbituric acid in approximately 800 ml of deionised water and then adjusting the pH at 8.6 by the addition of 0.2 molar hydrochloric acid; the volume of the buffer solution is then made up to 1000 ml by means of deionised water.

The antiserum is prepared by generating antibodies in goats as described above; the diluted composition is preserved by the addition of 0.1% sodium azide.

0.1 molar sodium hydroxide solution is brought on a Sephadex column G 25. When the resin has swollen, the excessive sodium hydroxide solution is decanted, after which 0.5 ml of $^{125}$I thyroxine (0.1μ Ci) solution in 0.1 molar sodium hydroxide solution is provided on the column. 0.1 ml of the patient's serum to be tested is then added and carefully mixed with the marked thyroxine solution. After having passed all the liquid through the column, 4 ml of the above-described barbital buffer solution are added. When the buffer solution has been completely passed through the column, 0.5 ml of the above-mentioned antiserum is pipetted in the column and 20 μl of the same patient serum. The liquids are carefully mixed and then passed through the column. After an incubation period of 1 hour, 4 ml of the barbital buffer solution are added to the column. After passing through the liquid the radioactivity of the column is measured in a gamma counter. The thyroxine concentration in the patient serum is then read from a standard curve so that an impression can be obtained of the thyroid function: see FIG. 1.

The standard curve has been obtained by performing the above-described processes with standard sera which have a known thyroxine concentration, namely 10 and 20 standardized thyroxine units (in μg), plotted against the radio-activity (in pulses "p"). In this figure "h.o.t.", "e.t." and "h.r.t." refer to the thyroid function and mean "hypothyroid", "euthyroid" and "hyperthyroid" respectively.

EXAMPLE 2

The processes as in Example 1 are carried out with the exception that instead of a Sephadex column a test tube is used to which antibodies are bound chemically on the inside: the so-called "coated tube" principle. Such tubes are marketed, for example, under the Tradename SPAC T4 RIA kit. The test tubes are suitable for an initial serum sample of 25 μl. The test method is carried out by carefully mixing the serum sample in the test tube with a $^{125}$I thyroxine solution and then decanting. After termination of the this process a second sample of patient serum is added in a quantity of 5 μl. After incubation in 1 ml of barbital buffer at a pH of 8.6 and decanting, the radioactivity of the tubes is measured. The thyroxine concentration of the patient's serum is finally read from the associated standard curve: see FIG. 2.

Figure 2:
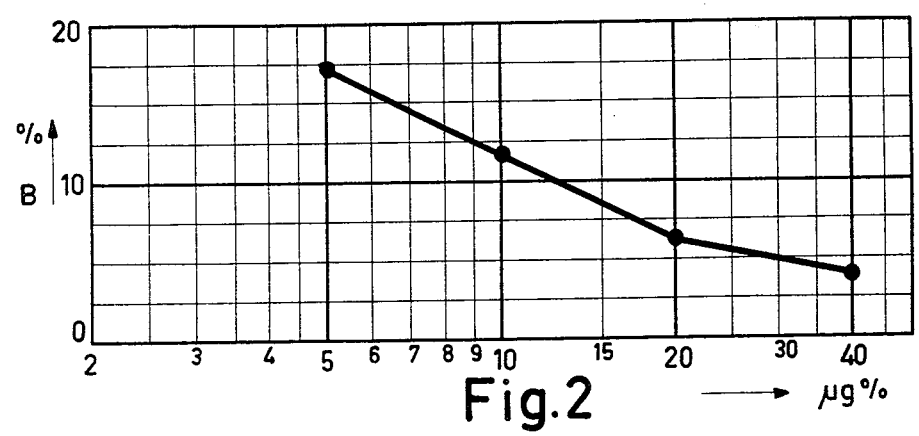
FIG. 2 illustrates a standard curve showing the relationship between the percentage of bound radioactivity versus the concentration of thyroxine in standard samples, when such standard samples are treated in accordance with the procedures of Example 2.

The standard curve shown in FIG. 2 has been obtained by performing the same processes with standard sera having a thyroxin concentration of 5, 10, 20 and 40 units. In this graph the percentage of normalized thyroxine units (in μg %) is plotted against the percentage of bound radioactivity (% B).

What is claimed is:

1. In a method for determining the thyroid function by an in vitro test using blood serum, in which test
   (a) a patient's blood serum sample is mixed with a solution containing radioactive thyroxine with a compound which liberates thyroxine from thyroxine-binding globulin;
   (b) the resulting test mixture is thereafter buffered with a buffering agent;
   (c) an antiserum is added to provide antibodies which bind a portion of the thyroxine present via a thyroxine-binding immunoreaction;
   (d) unbound thyroxine is thereafter separated from the thyroxine bound to antibodies; and
   (e) the relative quantities of unbound and bound thyroxine are thereafter determined by measurement of radioactivity;

the improvement which comprises adding to the test mixture after buffering an additional sample of the patient's blood serum, said additional sample being smaller in quantity than that of the patient's blood serum sample initially utilized.

2. The improved method of claim 1 wherein the additional sample of patient's blood serum added to the test mixture is added in an amount which is about 10% to 60% of the volume of the initial blood serum sample utilized.

3. The improved method of claim 1 or 2 wherein the separation of bound from unbound thyroxine in the test mixture is effected by contacting the test mixture with activated charcoal, polyethylene glycol or an ion exchange resin or by precipitating bound thyroxine with a second antibody, with ethanol or with ammonium sulphate.

4. The improved method of claim 1 or 2 wherein the separation of bound from unbound thyroxine in the test mixture is effected by passing said test mixture through a column containing dextran.

5. The improved method of claim 1 or 2 wherein the separation of bound from unbound thyroxine in the test mixture is effected by conducting the thyroxine-binding immunoreaction in a test tube having the thyroxine-binding antibodies adhering to the inside surfaces of the test tube.

* * * * *

UNITED STATES PATENT AND TRADEMARK OFFICE
CERTIFICATE OF CORRECTION

PATENT NO. : 4,271,141
DATED : June 2, 1981
INVENTOR(S) : Wilhelmus T. Goedemans It is certified that error appears in the above—identified patent and that said Letters Patent is hereby corrected as shown below:

Column 2, line 59, "of", first occurrence, should read -- to --.

Signed and Sealed this

Twenty-second Day of December 1981

|SEAL|

*Attest:*

*Attesting Officer*

GERALD J. MOSSINGHOFF
*Commissioner of Patents and Trademarks*